United States Patent [19]

Le Blanc et al.

[11] 4,044,606

[45] Aug. 30, 1977

[54] SENSING THICKNESS OF A THIN BODY DISPOSED BETWEEN TWO DIVERSE SURFACES

[76] Inventors: Lester Robert Le Blanc, 80 Highland Ave., Narragansett, R.I. 02882; Foster Hugh Middleton, Curtis Corner Road, Peace Dale, R.I. 02879

[21] Appl. No.: 695,144

[22] Filed: June 11, 1976

[51] Int. Cl.² ............................................ G01N 29/00
[52] U.S. Cl. ..................................................... 73/67.7
[58] Field of Search ................. 73/67.7, 67.8 R, 67.85, 73/67.9; 340/1 L, 1 R

[56] References Cited

U.S. PATENT DOCUMENTS

| | | | |
|---|---|---|---|
| 3,260,105 | 7/1966 | McNulty | 73/67.9 |
| 3,267,416 | 8/1966 | Morse | 73/67.7 X |
| 3,616,682 | 11/1971 | Golis et al. | 73/67.7 |
| 3,690,154 | 9/1972 | Wells et al. | 73/67.9 |
| 3,827,287 | 8/1974 | Boggs et al. | 73/67.8 S |
| 3,930,404 | 1/1976 | Ryden | 73/67.8 R |

*Primary Examiner*—James J. Gill
*Attorney, Agent, or Firm*—Albert P. Davis

[57] ABSTRACT

The thickness of a layer of oil on water is obtained in digital form, which in one embodiment is recorded on a visually identifiable analog type display chart. An underwater ultrasonic transducer arrangement produces and receives pulses, which are digitalized and processed in a digital computer for thickness calculation and organization for the display. To handle a wide range of signal conditions that need be detected at various interfaces, such as water to oil and the oil to air, a dynamic threshold is computed that permits the detection and processing of signals appearing at two diverse interfaces in conventional signal processing circuits that therefore can handle a large range of different signal conditions, thus permitting measurement of the thickness of a liquid layer of oil on the surface of water. The thickness of other fluids interposed between fluids having dissimilar acoustical properties can also be obtained.

7 Claims, 6 Drawing Figures

SENSING THICKNESS OF A THIN BODY DISPOSED BETWEEN TWO DIVERSE SURFACES

This invention relates to acoustic wave interface sensing equipment and processes and more particularly it relates to the measurement of the thickness of a layer of substance disposed at opposite surfaces between two bodies of diverse substance, such as an oil layer between water and air surfaces.

BACKGROUND

It has been well known to detect interfaces between two liquids such as oil and water or water and air by ultrasonic methods. Exemplary of such art is U.S. Pat. No. 3,520,186 issued to G. L. Adams et al. July 14, 1970. However, such prior art does not afford suitable techniques for measuring the distance between two interfaces such as for example to indicate the thickness of a layer of oil on top of water where there is on one side on oil-water interface and on the other side an oil-air interface.

In many operations in the petroleum industry it becomes necessary to measure the thickness of an oil layer floating on a body of water. These include oil tanks on tankers where sea water is commonly pumped into and out of tanks for ballast purposes. A similar application on a tanker is a settling or separation tank, from which separated water is pumped overboard.

A similar need to measure an oil layer thickness arises on the high seas in the event of accidental discharge of oil or as a result of ship collisions. Some machines whose function it is to clean up spilled oil in rivers, harbors, coastal regions, near refineries, etc., require a layer thickness sensor to function properly.

Deficiencies of the prior art techniques for this purpose are accentuated by various technical problems presented in measurement by ultrasonic sensing of the thickness of layers of oil on water for example. Perhaps the most important problem to be overcome is the necessity to work with a very large range of signal amplitudes, so that sensitive equipment is necessary to process weak signals which therefore is readily overloaded with strong signals. The interface between water and oil provides a weak reflection of ultrasonic pulses that must be detected and processed reliably in the presence of much larger signal amplitudes produced for example at the oil and air interface. Furthermore under dynamic conditions where the surfaces are changing such as when oil is being cleaned off the water surface or there is wave activity, successive signal pulses may encompass a very wide range of signal amplitude variations ranging from noise levels upward.

A further significant deficiency in the prior art is the signal to noise improvement factor necessary to provide meaningful measurements. Bubbles can give false signals or absorb signal strength for example. Waves can cause reflection angles to change with resultant signal deterioration. Dynamic film conditions can cause variations of thickness that may need be distinguished from noise conditions.

Even in the display of measurements many heretofore unsolved problems exist. The resolution need be good enough to distinguish signals from noise, and to display very thin film thicknesses with accurate dimensioning. Preferably such display to be on the same display medium that will handle a wide range of thickness dimensions automatically without intervention or adjustment by the operator.

OBJECTS OF THE INVENTION

It is therefore a general objective of this invention to provide feasible equipment and processes for ultrasonically measuring the thickness of a layer such as oil disposed between two diverse substances such as water and air.

A more specific object of the invention is to provide processes and apparatus for operating dynamically over a wide range of signal conditions encountered in the ultrasonic sensing of an oil layer on water by measuring the time between two discreet reflections of an acoustic pulse from water-oil and oil-air surface interfaces.

Another object of the invention is to provide visual display means translating the time between two detected acoustic pulses at interfaces on both sides of a layer under observation into meaningful dimensional format that produces good resolution for both thick and thin film dimensions.

THE DRAWINGS

FIG. 1 is a block system diagram of the system and process afforded by the invention to measure the thickness of a layer of oil by measurement of the time between portions of an acoustic pulse reflected from interfaces on opposite sides of the layer surface, FIG. 2 is a graph showing a typical signal configuration following a transmitted pulse that represents a portion of a visual display scan period, FIG. 3 is a display showing a dot matrix arrangement by which the data display is formed, FIG. 4 is a block diagram of the interface equipment between a sonar system and digital computer processing the received sonar signals, FIG. 5 is a block representation of the operational mode of the invention in storing signals for presentation to a scan type recorder display, and FIG. 6 is a typical program chart for processing digital signals in a computer for organization in display form and for generating a dynamic threshold signal.

DETAILED DESCRIPTION

Figure 1:
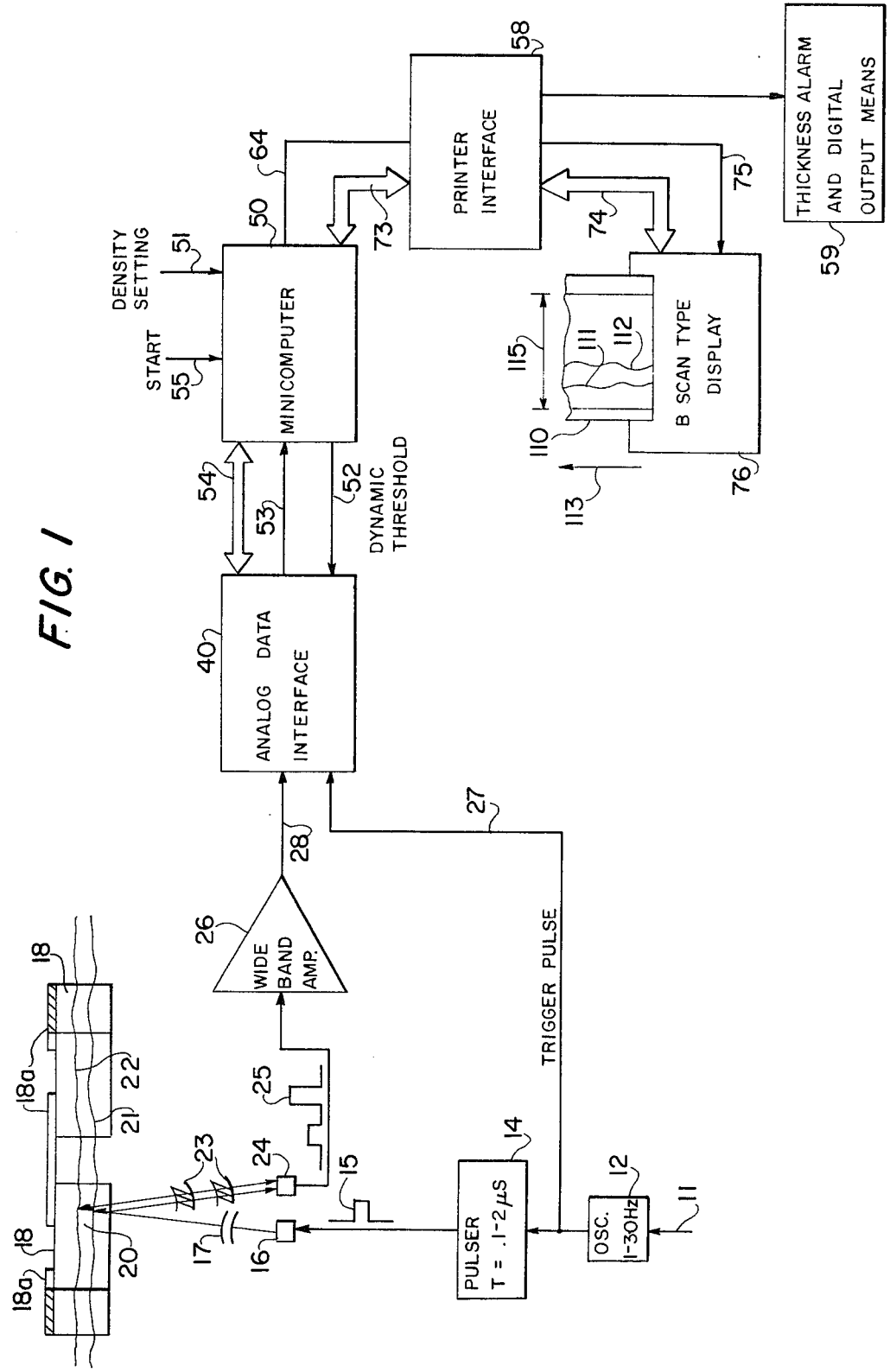

FIG. 1 is intended to show the comprehensive interactions of the layer thickness measurement system afforded by this invention. Thus a sonar system comprises a pulse repetition rate oscillator 12 providing a frequency in the order of 10 Hz set at lead 11 by an operator. The output serves to fire a sonar pulser 14 providing sharp power pulses 15 of duration T of the order of 1 microsecond. These pulses actuate a transducer 16 to produce a corresponding acoustic pulse 17 with a narrow beam width of about 2°. The transducer arrangement is held in place by structure (not shown) beneath a plurality of spaced floats 18 secured in a generally annular form by plates 18a which encompasses a large enough surface area to track with the waves and average out the effect of wave motion.

When a layer of oil 20 rides on top of the water, it presents two interfaces to the acoustic pulse 17, namely the water to oil interface 21 and the oil to air interface 22, from which reflected acoustic pulses 23 are derived for detection in receiver transducer 24. The resulting electrical pulses 25 are amplified at 26 to produce an analog scan signal timed with the oscillator trigger pulses on line 27 to constitute output signal data from the sonar system portion of the invention. Sonar equipment of this type is of itself conventional. However a novel system for the processing of the two reflected pulses 23 to derive therefrom a measurement of oil thickness by translation of the time between the reflected pulses is provided by the present invention. Since the rate of travel of acoustic energy in oil or other layer substance is known, the time differential provides a measurement of film thickness. Thus, the transducer 16 could be directed downwardly for example to measure the thickness of a mud layer at the bottom.

Figure 2:
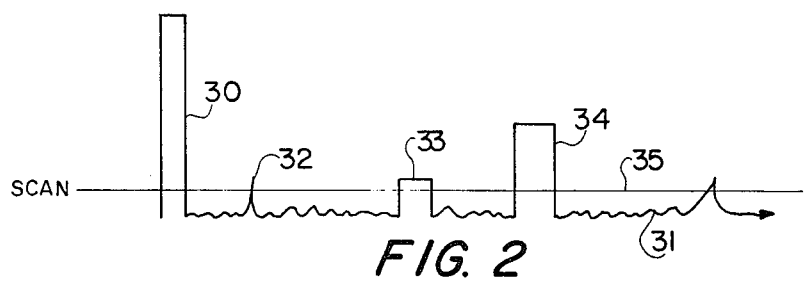

The analog data interface 40 serves to prepare the analog data signals on lead 28 for digital processing in the digital computer 50. The input trigger pulse signal at 27 indicates a time reference frame for the start of a data scan with pulse 30 as shown in FIG. 2. Then the analog data 31 is developed by receiving transducer 24 including noise spikes such as 32 and reflected signal pulses 33 and 34 respectively from the water to oil and oil to air interfaces.

It is significant in this invention that the threshold level 35 set for passing signals is dynamically variable. In this embodiment the computer 50 processes the signal pulses appearing above the threshold as introduced to the computer on line 53 to service as a function of signal density a threshold signal on computer ouput lead 52 that matches a manually set threshold level 51 to retain the appropriate signal "hit density." Status information passes each way between interface 40 and computer 50 over cable 54, to aid in the control functions.

Figure 4:
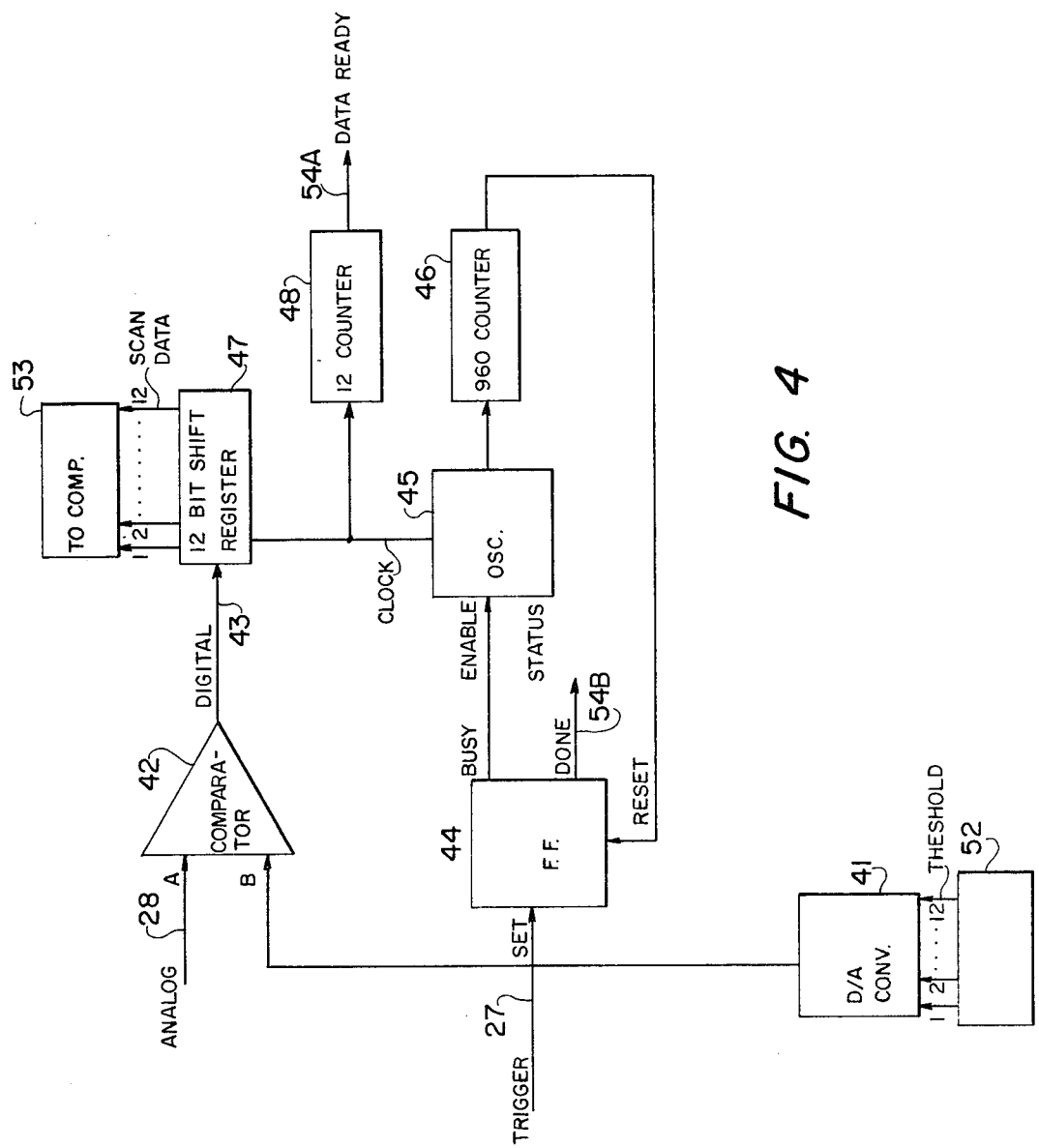

For a better understanding of the interface function FIG. 4 may be consulted. Throughout the various figures, like reference characters are used for similar elements to facilitate comparison. Thus the input and output leads 27, 28, 52, 53 and 54 are identified.

The threshold signal from the computer comprises a set of twelve digital on-off channels which are converted in digital to analog converter 41 to a threshold bias input voltage for comparator 42, which passes analog signals at lead 28 only when they exceed the amplitude of the threshold setting. Thus output digital signals are provided at line 43 for each scan (FIG. 2) initiated at the time of the trigger pulses on line 27.

Each scan trigger pulse readies the interface system by setting control flip-flop 44, which turns on adjustable 0.10 to 4.4 $MH_z$ clock oscillator 45 for 960 counts registered in counter 46 before the flip-flop 44 is reset for another 10 ms to 0.25 ms scan depending on the setting of clock oscillator 45 to produce a "done" status signal to the computer at lead 54B. Oscillator 45 output pulses are used as a clock for the computer and as a sample for sampling each of the reflected sonar echo pulses (33, 34 FIG. 2) of the data scan several times. This gives a better output signal to noise ratio accentuating each reflected pulse thereby improving the dynamic range of detection when waves and bubbles, etc., are encountered.

Thus each oscillator cycle causes 12 bit shift register 47 to retain the signal samples for transfer to the computer as digital scan data for each cycle in 80 groups of 12 bits or 960 bits as identified by counter 46. Each shift register load of 12 bits is transferred into the computer by command of twelve counter 48. This produces a matrix array of digital on-off signals for each scan as outlined in FIG. 3 with 12 scan channels over an 80 bit sweep resolution for a total sweep capacity of 960 bits.

It is noted that other data display forms may be used, for example, to print out periodically from computer 50 (FIG. 1) by way of interface 58 at output device 59 a digital reading of the time computed between the reflected pulses 33 and 34 in terms of layer thickness dimensions, or a threshold alarm signal when the layer passes a predetermined check dimension which can be used to control an external device such as a bilge pump. It is also possible to drive an analog meter with an averaged constant voltage or current pulse turned on for that time interval between the two reflected pulses 33, 34.

Simple status signals are not detailed since they can be varied as desired by those skilled in the art. However the operator may have a start control button 55 which readies all the equipment for operation by means of appropriate status signals such as connection of power.

Figure 5:
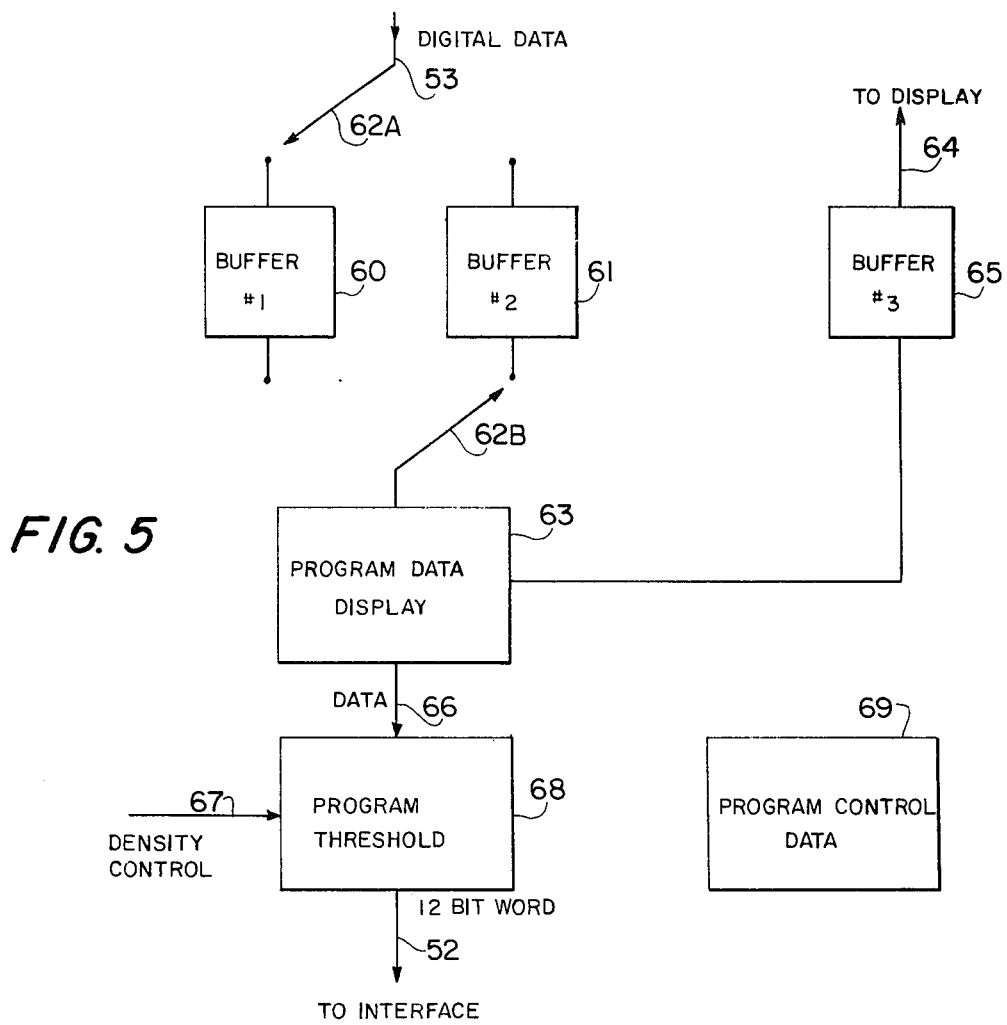

As may be seen from the function system representation of FIG. 5, the computer 50 serves to organize data for use in the display system and also serves to derive the dynamic threshold signal. Thus input digital data at lead 53 is stored alternately in two buffer memory sections 60 and 61 by computer programmed switch 62. This permits a complete array of 960 bits to be transferred into buffer position 61 so that buffer position 61 can be filled.

The computer is programmed to rearrange the data of the buffer being read out (61) for use in the display by way of output line 64 via display buffer section 65. Also the data is processed through data line 66 to threshold operation 68, where the program derives the threshold 12 bit word at line 52 as a function of the density set by the operator by control 67. Further the computer has a program 69 for processing data from input to output through the computer.

Figure 6:
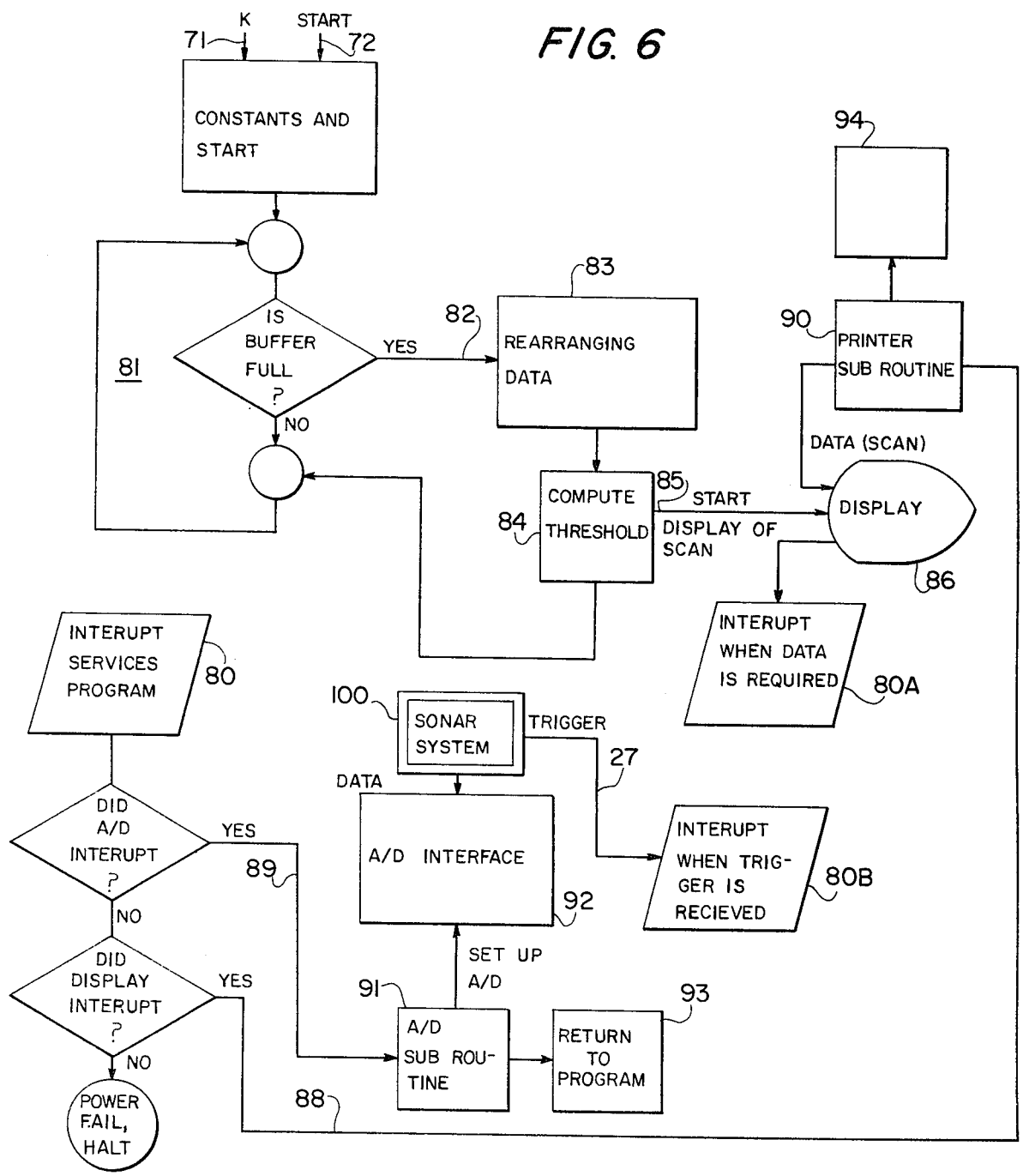

While computer programming is well known in the art and can be done to achieve the foregoing functions, the diagram of FIG. 6 can be referred to as a standard program instruction diagram for indicating the pertinent program steps.

The program has constants $k$ entered as shown at 71 by the operator and is started manually at 72. The main program loops until a buffer flag indicates one buffer 60, 61 is full and then proceeds to unscramble the data and load display output buffer 65. Simultaneously a hit density signal is prepared. The main program starts the display scan head in printer 76 (FIG. 1) and the scan head signals the computer when ready for new data by an interrupt signal 80 (FIG. 6), all on status and control lines 73 and 74 (FIG. 1) with data transfer on lines 64 and 75.

The "buffer full" decision subroutine 81 provides a signal 82 for starting the data rearranging subroutine 83 and the threshold computations 84 providing a start signal 85 for the display scan subroutine 86, which provides the interrupt signal 80A when the display requires data.

The service program decides whether the display interrupted the program at 88 or the A/D did at 89. Respectively these signals trigger the printer subroutine 90 or the A/D subroutine at 91 which keeps track of the status of the buffers and provides the A/D interface board 92 with the proper memory location for a direct memory access to receive new data from the sonar system 100. Also the A/D subroutine calculates a threshold level and provides the A/D converter with the threshold level.

The trigger pulse line 27 interrupts the program with a signal 80B when a new scan starts. The signal at 93 returns to the program when the A/D subroutine is finished, as does the corresponding signal 94 when the printer subroutine is finished. The computer 50 (FIG. 1) may be for example a standard Fabri-Tek MP 12 minicomputer which provides direct memory access for digital data 53.

Figure 3:
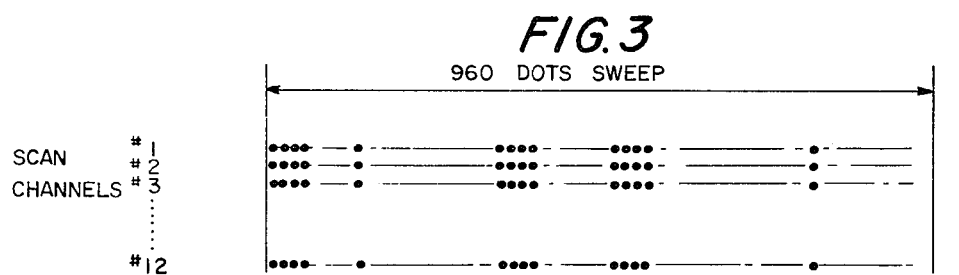

The visual display is developed on a B scan type of display graph 110 with corresponding oil and air reflection signals 111, 112 displayed along the time axis of the chart moving in the direction of arrow 113, as each scan crosses the chart from left to right as indicated at 115 with the 12 scan heads in parallel corresponding to the matrix array of FIG. 3. This gives a dynamic visual indication of the layer thickness between the two signal lines which are selected for proper density by control 51 via the automatic dynamic density control feature. If no oil layer is present, the air reflection signal 112 of the main surface will always be seen.

It is desirable for some purposes to build in a sub-program step to sense that both signals are present. The presence or absence of interface signals can be calculated much the same way as the threshold signal is derived by signalling the density expected when two signals (33, 34 FIG. 2) are sampled the required times over their entire duration. The sub-program will also maintain a tracking record of the location of the last interface signals and by this means determine whether a new interface signal is within proper bounds. If not, the interface signals will be rejected as erroneous. If a preset number of rejections occur consecutively, the program will disregard the last tracks and search for new interface signals and set up new tracks. This arrangement provides a high resolution interface measurement at fast data rates for ready visual observation on other forms of conventional display such as a direct numerical readout. Other scanners or print arrangements can be used but an Inforex dot matrix plotter advantageously produces a simple fast printout from a 12 channel printout scan which is about 250 cm in width and which is comprised of individual binary signal dots from the stored computer data.

In normal facsimile type displays, manual adjustment of threshold is accomplished by an observer balancing the black to white regions of the record to suit his taste. That is, if the sensitivity is set too high, a dark and detail-void record results. Conversely, setting the sensitivity, or the marking level too low produces a pale and detail-void display. In this thickness sensor, the computer simply keeps track of the marking level and changes the threshold as required. The final display then can have a relatively constant contrast appearance, even though the oil layer condition changes markedly.

What is claimed is:

1. Apparatus for indicating the thickness of a layer of oil floating on a moving body of water comprising in combination, acoustic pulser apparatus comprising an ultrasonic transducer adapted to be positioned beneath the surface of said body of water and adapted to repetitively transmit discrete pulses of wave energy in a narrow beam at a predetermined repetition frequency from said body of water along a path through said layer of oil and into the atmosphere thereabove, a float for supporting said transducer in said body of water, said float being of a size to encompass a large enough surface area to track with waves on the oil-water surface to average out the effect of wave motion, acoustic receiver apparatus adapted to detect noise and reflected pulses from said beam including some discrete signals reflected from the oil-water interface and some discrete signals reflected from the oil-atmosphere interface, dynamic threshold apparatus for rejecting reflected energy and noise having a predetermined amplitude below the amplitude of discrete signals reflected from the oil-water interface, and means for translating the time span between the pulses reflected from the two said interfaces into an indication of the thickness of said layer of oil.

2. Apparatus as defined in claim 1 wherein said threshold apparatus includes a digital computer programmed to process the reflected pulses and noise to establish thereby dynamically as a function of the noise and reflected pulse density a signal representative of a dynamic threshold value for rejection of reflected pulses and noise and a manual "hit density" setting for selectively varying the density at which the said threshold is established.

3. Apparatus as defined in claim 2 wherein the means indicating thickness produces a visual display.

4. Apparatus as defined in claim 3 wherein the visual display comprises a scan type display with all reflected pulses having an amplitude above the threshold amplitude being produced on a single scan as a dot pattern.

5. Apparatus as defined in claim 4 wherein the means translating the time span includes a digital computer, wherein the computer is programmed to store a plurality of reflected pulses, and the display records the stored pulses on a scan cycle initiated by the computer.

6. Apparatus as defined in claim 4 wherein the means translating the time span includes a digital computer, wherein the computer is programmed to assemble and store a plurality of reflected pulses, and the display has a multiple line scan which records the stored pulses in the multiplicity of lines on a scan cycle initiated by the computer.

7. Apparatus as defined in claim 4 wherein the means translating the time span includes a digital computer, a comparator and a shift register and the computer is programmed to interact with said comparator and said shift register to provide a multiplicity of sequential single bit threshold decisions relating to the signals to be stored in the computer in a parallel manner.

* * * * *